United States Patent [19]

Klostermark

[11] 4,164,814
[45] Aug. 21, 1979

[54] PERSONAL USE DEVICE FOR REMOVING TARTAR FROM THE INNER SIDE OF TEETH

[76] Inventor: Bernt Klostermark, Smedsbacksgatan 3B, 115 39 Stockholm, Sweden

[21] Appl. No.: 819,983

[22] Filed: Jul. 28, 1977

[30] Foreign Application Priority Data

Aug. 6, 1976 [SE] Sweden .................................. 7608825

[51] Int. Cl.² .......................... A61C 3/00; A61C 15/00
[52] U.S. Cl. ........................................ 32/69; 32/40 R; 32/32; 32/50
[58] Field of Search ................ 15/105; 32/69, 32, 50, 32/40 R; 350/308, 309, 301; 128/10, 304; 88/104; 85/8.8; 132/84 C

[56] References Cited

U.S. PATENT DOCUMENTS

| 726,895 | 5/1903 | Franklin | 32/69 |
| 727,483 | 5/1903 | Street | 32/69 |
| 2,434,311 | 1/1948 | Dean | 32/69 |
| 2,552,134 | 5/1951 | Berliner | 32/50 |

*Primary Examiner*—Louis G. Mancene
*Assistant Examiner*—Michael J. Foycik
*Attorney, Agent, or Firm*—Strauch, Nolan, Neale, Nies & Kurz

[57] ABSTRACT

A personal dental care device including a dentist mirror and a flat, stiff tooth scraper projecting substantially perpendicular to the mirror, located at the edge of the mirror and either fixed on the mirror frame or rotatably positionable around the periphery of the mirror. There are several embodiments for mounting the tooth scraper adjacent the mirror.

7 Claims, 6 Drawing Figures

U.S. Patent  Aug. 21, 1979  4,164,814
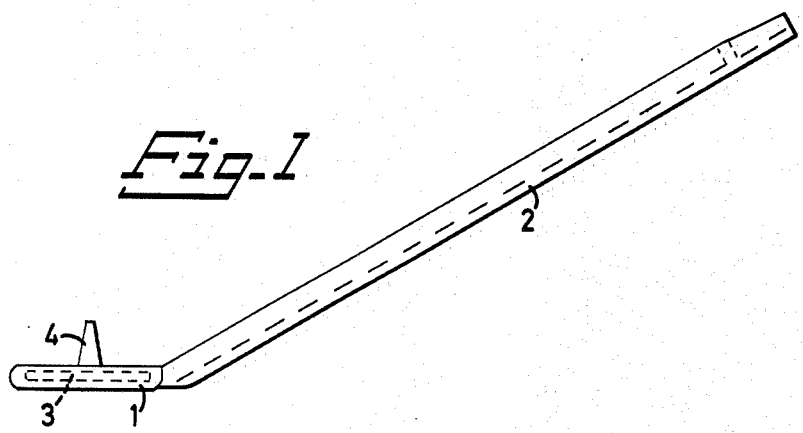
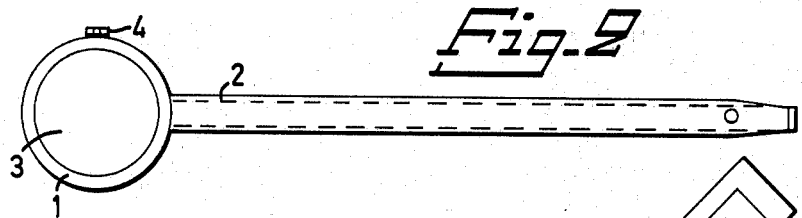
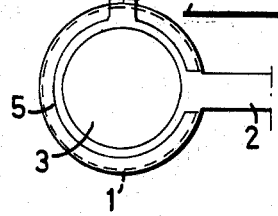
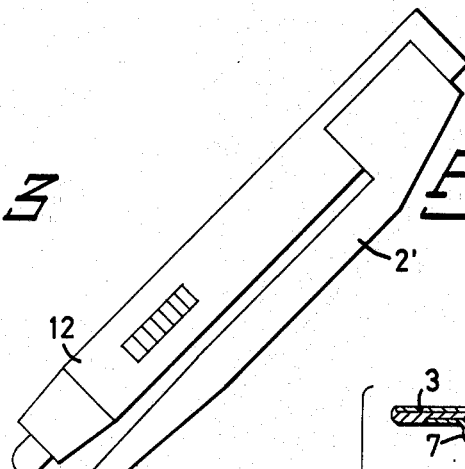
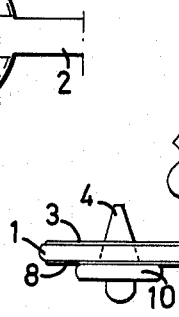
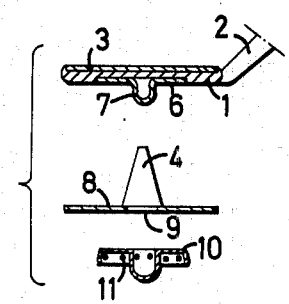
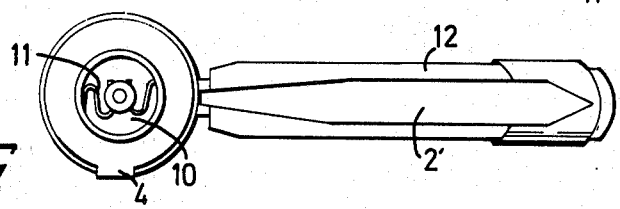

PERSONAL USE DEVICE FOR REMOVING TARTAR FROM THE INNER SIDE OF TEETH

BACKGROUND OF THE INVENTION

The present invention relates to a device for removing tartar from the inner side of a teeth row, used during personal dental care in the home. In the recent years personal dental care has been regarded as more and more important than before. There are many facilities commercially available today for this purpose. For a long time it has been a general practice to brush the teeth regularly for both old and young people.

To motivate and encourage a careful personal dental care in the home the dentists also recommend inspection of especially the back sides of the teeth, so that any tendency of decay can be discovered and if possible removed as soon as possible. However, this must be done either at the dentist or at a dental hygienist, who will most often scrape off the tartar. However, it is often a problem for the patient that a too long time may pass until the next visit to the dentist.

Consequently, it would be very advantageous if caries or decay removal could be incorporated in the personal dental care in the home. However, it is too difficult to handle some kind of tooth scraper on the inner side of a teeth row with one hand and to hold a so called dentist's mirror inside of the same teeth row with the other hand, and at the same time to regard the picture of the teeth to be treated reflected from the dentist's mirror in a mirror located in front of the mouth.

It is an object of the present invention to highly facilitate and make more effective the removal of tartar from the inner side of a teeth row.

According to the invention, this is accomplished by a tooth scraper of preferably metal, nylon or some other plastic material, which is arranged on the edge of and extending above the plane of a dentist's mirror known per se, said tooth scraper extending substantially perpendicularly to the plane of said dentist's mirror. Furthermore, said tooth scraper can suitably be adjusted by rotation to an optional position on the edge of the dentist's mirror.

The invention will be illustrated by some embodiments shown as examples in the attached drawing.

FIGS. 1 and 2 show a side view and a plan view respectively of a manual dentist's mirror provided with the device according to the invention.

FIG. 3 shows a plan view of a part of a dentist's mirror having a modified construction for the device according to the invention.

FIG. 4 shows the parts of the device according to the invention in section and having another modified construction.

FIG. 5 shows a side view of a dentist's mirror having the parts according to FIG. 4 mounted thereon.

FIG. 6 shows the embodiment of FIG. 5 as seen from below.

A known manual dentist's mirror according to FIGS. 1 and 2, comprises a frame 1, a handle 2 extending therefrom at a suitable angle, and a mirror 3 mounted in the frame 1. At a certain place on the edge of the frame 1 a suitably pointed tooth scraper 4 is fastened in some suitable way. For example it can be made as a part of the frame, if this is of metal. Said tooth scraper 4 extends a bit above and substantially perpendicular to the plane of the mirror 3. It can suitably be made of a blade of metal or another material, for example nylon or some other plastic material, that is stiff enough but also resilient, if the pressure thereon during the scraping should be greater than what is normally intended for the tooth scraper.

The device described is simple and easy to handle, and is used in the following easy way. The handling person sits or stands in front of a mirror and, holding the device 1-4 by one hand, moves it into the mouth and scrapes the back sides of the teeth by the scraper 4. The particular spot to be scraped is reflected in the mirror 3 and from there to the mirror in front of the mouth. Thereby, the scraping procedure can be easily regarded and the tooth scraper 4 can be easily held and moved to the places that need to be scraped. By the device according to the invention the whole scraping procedure becomes very simple and gives a very good result.

If the frame 1 is made of metal or a hard enough plastic material, the tooth scraper 4 can be made in one piece therewith. In other cases the tooth scraper forms a separate part fastened to the frame 1. FIG. 3 shows a separate fastening of the tooth scraper 4. A disc 5 of metal, nylon or some other suitably hard plastic material is arranged on the back side of the mirror frame 1 and provided with a bent up edge substantially along its circumference, a part of said bent up edge forming a tooth scraper 4 and the rest of the edge being bent around the frame 1 to retain the disc 5 to the frame.

The position of the tooth scraper 4 can of course be anywhere else along the edge of the frame than the position shown in FIGS. 1-3. In the construction according to said figures it is presumed that the whole device should be held in the right hand. If however, the device is to be held in the left hand, the tooth scraper should be positioned on the radially opposite part of the frame. Therefore, according to the invention it is advantageous if the construction is such, that the scraper 4 can be rotated along the edge of the frame to be adjusted into any position desired or necessary along said edge.

FIGS. 4-6 show an example of such a rotatable tooth scraper. As can be best seen in FIG. 4, a base plate 6 is mounted on the back side of the frame 1 such that its back surface is in level with the back surface of said frame 1. Centrally on its back side the base plate 6 is provided with a connection pin 7, for example a pin with a head. On its outer edge, a plane circular plate 8 is provided with the tooth scraper 4, and at its central part it is provided with a hole 9, the diameter of which being the same as the greatest diameter of the connection pin 7. Thus, the plate 8 can be mounted on the base plate by the connection pin 7 being inserted in the hole 9. A retaining means 10 is arranged to be thread on to the connection pin 7. It is provided with springs 11 for engagement with the connection pin. Hereby, the retaining means 10 is removably fastened to the connection pin 7. The connection pin and the retaining means can be of the same kind as press-studs for clothes and the like, but any suitable kind of connection means may be used.

All of the parts 6-10 can be made of some other material than metal, for example nylon or some other plastic material, that is enough hard and resilient at the same time, so that for example the tooth scraper will be sufficiently hard and the retaining means will be elastic enough to removably engage around the connection pin without any springs 11.

FIGS. 5 and 6 show the parts of FIG. 4 mounted together. The plate 8 which is provided with the tooth scraper 4, is mounted on the connection pin 7. Thereafter, the retaining means 10 has been thread on and brought into engagement with the connection pin 7. Hereby the plate 8 is pressed against the back side of the frame 1 and the base plate 6, which is in level with the frame. The plate 8 is consequently retained by friction engagement in position, and its position can be adjusted by the plate being rotated around the pin 7, so that the tooth scraper 4 can have any desired position at the edge of the frame. Hereby the device can also be adapted for a right- or lefthanded person.

As can be seen in FIGS. 5 and 6, a battery powered lighting means 12 can be arranged on the handle 2 to illuminate the mirror, which reflects the light to the spot to be treated on the teeth.

The invention is not to be limited to the embodiments described above and shown in the drawings, since these can be modified within the scope of the invention. For example the outer configuration of the tooth scraper can be modified. The tooth scraper can be bent in its longitudinal direction. The means for mounting the tooth scraper on the mirror fixedly, removably and/or rotatably can be varied, especially depending on if the tooth scraper is made as a separate part, for example of the kind to be used only once and then thrown away, or if it is made in one piece with the mirror. In the last case the connection pin can be made in one piece with the frame, and the retaining means can be made in one piece with the plate carrying the tooth scraper.

What I claim is:

1. A combination mirror and tooth scraper for use as a personal dental care device for removing tartar from the inner side of a teeth row comprising a dentist mirror with mirror frame and handle, an elongate flat tooth scraper made from stiff and slight resilient material secured on the frame adjacent the edge of and projecting up above the plane of the mirror, said tooth scraper planar from being substantially perpendicular to the plane of the mirror.

2. A device according to claim 1, wherein means securing said tooth scraper comprises a disc and said tooth scraper is a bent up part of said disc, said disc having its periphery curved around the edge of the mirror frame.

3. A device according to claim 2, wherein said tooth scraper disc has a fit on said frame enabling it to be adjusted to an optional position by rotation around the frame of the mirror.

4. A device according to claim 1, wherein the means securing said tooth scraper comprises: a plate with said tooth scraper being a bent up part of said plate; and retaining means rotatably mounts said plate to the mirror frame under said mirror.

5. A device according to claim 4, said securing means further comprising a connection pin with a head, said pin being mounted centrally on the back side of the mirror frame, the plane of the back surface of the base plate being parallel with the plane of the back side of the frame; said plate is provided with a central aperture enabling said plate to be mounted over said connection pin; and said retaining means is removably engaged around said connection pin and against said plate whereby the plate carrying the tooth scraper will be pressed against the under side of the mirror frame.

6. A device as defined in claim 4, wherein said plate and tooth scraper portion are made from a stiff, slightly resilient plastic.

7. A device as defined in claim 6, wherein said plastic is nylon.

* * * * *

UNITED STATES PATENT AND TRADEMARK OFFICE
CERTIFICATE OF CORRECTION

PATENT NO. : 4,164,814
DATED : August 21, 1979
INVENTOR(S) : Bernt Klostermark

It is certified that error appears in the above-identified patent and that said Letters Patent are hereby corrected as shown below:

Column 4, line 3, change "from" to --form--.

Signed and Sealed this

Eighteenth Day of March 1980

[SEAL]

Attest:

SIDNEY A. DIAMOND

Attesting Officer

Commissioner of Patents and Trademarks